United States Patent [19]

Hsu et al.

[11] Patent Number: 5,256,668
[45] Date of Patent: Oct. 26, 1993

[54] AMINOPYRIMIDINE DERIVATIVES AS ANTIVIRAL AGENTS FOR RESPIRATORY SYNCYTIAL VIRUS

[75] Inventors: Kuo-Hom L. Hsu, Fort Washington, Pa.; Daniel M. Teller, Columbus, Ohio; Alan R. Davis, Wayne; Michael D. Lubeck, Glenmoore, both of Pa.; Jehan F. Bagli, Princeton, N.J.

[73] Assignee: American Home Products Corporation, New York, N.Y.

[21] Appl. No.: 32,065

[22] Filed: Mar. 17, 1993

[51] Int. Cl.$^5$ ............................................. A61K 31/505
[52] U.S. Cl. .................................................... 514/269
[58] Field of Search ........................................ 514/269

[56] References Cited

U.S. PATENT DOCUMENTS

| | | | |
|---|---|---|---|
| 4,505,910 | 3/1985 | Bagli | 514/26 |
| 4,617,393 | 10/1986 | Bagli et al. | 544/319 |
| 4,980,355 | 12/1990 | Zondler et al. | 514/256 |
| 5,002,949 | 3/1991 | Peseckis et al. | 514/256 |

OTHER PUBLICATIONS

Belshe and Hay, J. Respiratory Diseases 10:552–561 (1989).

Bagli et al., J. Med. Chem. 31, 814–823 (1988).

Primary Examiner—Frederick E. Waddell
Assistant Examiner—Russell Travers
Attorney, Agent, or Firm—R. F. Boswell, Jr.

[57] ABSTRACT

Antiviral activity against respiratory syncytial virus has been found in some substituted 6-aminopyrimidines having the formula:

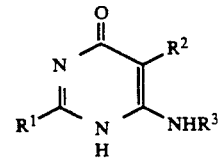

wherein $R^1$ is lower alkyl, preferably methyl or t-butyl, $R^2$ is halogen or cyano, and $R^3$ is $C_1$–$C_6$ alkyl or —$(CH_2)_n R^4$ where n is 1 or 2 and $R^4$ is phenyl, phenyl substituted by lower alkoxy, lower alkyleneoxy, bromo, or 3,4-methylenedioxy; 3 or 4-pyridinyl, pyridinyl substituted by cyano or bromo, thienyl, or di-($C_1$–$C_6$ alkyl)amino.

10 Claims, No Drawings

AMINOPYRIMIDINE DERIVATIVES AS ANTIVIRAL AGENTS FOR RESPIRATORY SYNCYTIAL VIRUS

FIELD OF INVENTION

This invention relates to antiviral activity found in some 6-substituted amino-4-pyrimidinone compounds. Belshe and Hay, J. Respiratory Diseases 10:552–561, 1989, hypothesize that the M2 protein of influenza virus and the SH protein of respiratory syncytial virus (RSV) may function as ion channels. The compounds used in the method of this invention have certain structural similarities to the known potassium channel opener, pinacidil (N-cyano-N'-4-pyridinyl-N''-1,2,2-trimethylpropylguanidine). Two of the compounds which had good antiviral activity against RSV were tested against influenza A and found to be inactive against the influenza A virus.

Respiratory syncytial virus (RSV) is a pneumovirus that causes respiratory infections. RSV is the single most frequent cause of serious respiratory disease in young children, often resulting in lower respiratory tract infections. (Volck, et al, Essentials of Medical Microbiology, 3rd ed., 1986, J. B. Lippincott Co., Philadelphia, p. 727). RSV infections are currently treated with ribavirin, a synthetic nucleotide that is administered intranasally as an aerosol.

DESCRIPTION OF THE INVENTION

The compounds useful in the method of this invention were synthesized for cardiovascular activity and are disclosed in U.S. Pat. Nos. 4,505,910; 4,617,393; 5,002,949 and in J. Med. Chem. 1988, 31, 814–823 and are herein incorporated by reference. The compounds are represented by Formula I below:

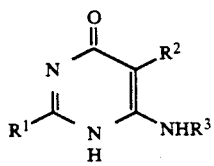

I wherein:
$R^1$ is $C_1$-$C_6$ lower alkyl;
$R^2$ is halogen or —CN;
$R^3$ is $C_1$-$C_6$ alkyl or —$(CH_2)_nR^4$ where n is 1 or 2 and $R^4$ is phenyl, phenyl substituted by 1 to 2 groups selected from lower alkoxy, lower alkenyloxy, halogen or 3,4-methylenedioxy;
pyridinyl, substituted pyridinyl where the substituent is selected from halogen or cyano, thienyl, or —$NR^1R^2$ where $R^1$ and $R^2$ are $C_1$-$C_6$ alkyl or —$NR^1R^2$ is a cyclic amine of 4 to 6 atoms;
or a pharmaceutically acceptable salt thereof.

By way of further definition of terms used above, $C_1$-$C_6$ alkyl includes straight and branched chain hydrocarbons, lower alkoxy is —O—($C_1$-$C_6$ alkyl), lower alkenyloxy is —O—($C_1$-$C_6$ alkenyl) where the alkenyl group may have one site of unsaturation, halogen is selected from fluorine, chlorine, bromine or iodine, and —$NR^1R^2$ defined as a cyclic amine of 4 to 6 atoms is selected from azetidine, pyrrolidine or piperidine.

The term pharmaceutically acceptable salt includes solvates, hydrates, acid addition salts and quaternary salts. The acid addition salts are formed from a Formula I compound having a basic nitrogen and a pharmaceutically acceptable inorganic or organic acid including but not limited to hydrochloric, hydrobromic, sulfuric, phosphoric, methanesulfonic, acetic, citric, malonic, fumeric, maleic, sulfamic, or tartaric acids. Quaternary salts are formed from a basic Formula I compound and an alkyl or arylalkyl halide, preferably methyl or benzyl bromide.

Preferred Formula I for use in this invention are those wherein $R^1$ is methyl or t-butyl, $R^2$ is bromo, chloro, fluoro or cyano, $R^3$ is 2-methylbutyl or —$(CH_2)_nR^4$ and $R^4$ is phenyl, 3-methoxy-4-(2-propenyloxy)phenyl, 5-bromo-2-methoxyphenyl, 3-thienyl, 3-pyridinyl, 4-pyridinyl, 3-thienyl, 3-pyridinyl, 4-pyridinyl, 5-bromo-3-pyridinyl, 5-cyano-3-pyridinyl, 3,4-methylenedioxyphenyl, dimethylamino, dipropylamino, or 1-pyrrolidinyl or a pharmaceutically acceptable salt thereof.

More preferred compounds for use in this invention are those wherein $R^1$ is t-butyl, $R^2$ is —CN and $R^3$ is 3-pyridinylmethyl or when $R^1$ is methyl and $R^2$ is —CN, then $R^3$ is selected from 2-(3-pyridinyl)ethyl, 2-(4-pyridinyl)ethyl, phenylmethyl, 2-dimethylaminoethyl, or 2-(1-pyrrolidinyl)ethyl; and when $R^1$ is methyl and $R^2$ is Br, $R^3$ is selected from 5-cyano-3-pyridinylmethyl, 2-(3-pyridinyl)ethyl, 2-dipropylaminoethyl, 3,4-methylenedioxyphenylmethyl, 3-thienylmethyl, 2-[3-methoxy-4-(2-propenyloxy)-phenyl]ethyl, 2-(5-bromo-2-methoxyphenyl)ethyl, 2-methylbutyl, or 5-bromo-3-pyridinylmethyl; or when $R^1$ is methyl and $R^2$ is Cl, $R^3$ is 5-bromo-3-pyridinylmethyl or a pharmaceutically acceptable salt thereof.

The compounds useful in this invention exist as tautomers in either the keto (Ia or Ib) or enol (Ic) forms as shown below, depending on the chemical environment. The keto structure Ia is used therein.

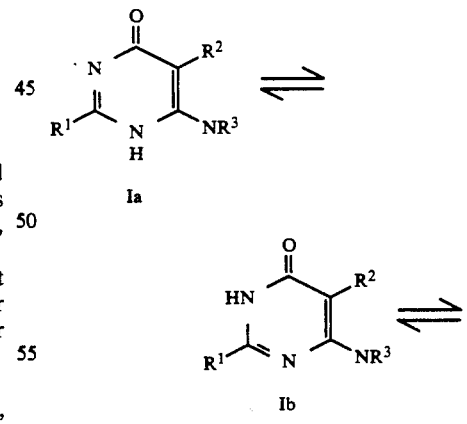

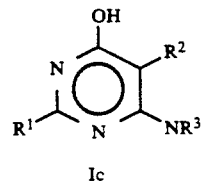

The useful compounds are summarized in the Table 1 below.

TABLE 1

Summary of structures of Anti-RSV Formula I Compounds

| Compound | $R^1$ | $R^2$ | $R^3$ |
|---|---|---|---|
| 1 | $CH_3$ | CN | $-CH_2CH_2-$(3-pyridyl) |
| 2 | $CH_3$ | Br | $-CH_2-$(3-cyano-pyridyl) |
| 3 | t-Bu | CN | $-CH_2-$(pyridyl) |
| 4 | $CH_3$ | CN | $-CH_2CH_2-$(pyridyl) |
| 5 | $CH_3$ | CN | $-CH_2-$phenyl |
| 6 | $CH_3$ | CN | $-CH_2CH_2N(CH_3)_2$ |
| 7 | $CH_3$ | CN | $-CH_2CH_2N$(pyrrolidinyl) |
| 8 | $CH_3$ | Br | $-CH_2CH_2-$(pyridyl) |
| 9 | $CH_3$ | Br | $-CH_2CH_2N(CH_2CH_2CH_3)_2$ |
| 10 | $CH_3$ | Br | $-CH_2-$(1,3-benzodioxol-5-yl) |
| 11 | $CH_3$ | Br | $-CH_2-$(thienyl) |
| 12 | $CH_3$ | Br | $-CH_2CH_2-$(2-allyloxy-3-methoxyphenyl) |
| 13 | $CH_3$ | Cl | $-CH_2-$(4-bromo-pyridyl) |
| 14 | $CH_3$ | Br | $-CH_2CH_2-$(3-methoxy-4-bromophenyl) |
| 15 | $CH_3$ | F | $-CH_2-$(pyridyl) |
| 16 | $CH_3$ | Br | $-CH_2CH_2N(CH_3)_2$ |
| 17 | $CH_3$ | Br | $-CH_2-$(4-bromo-pyridyl) |

DETAILED DESCRIPTION OF THE INVENTION

The antiviral activity against respiratory syncytial virus was determined in HEp-2 cells seeded in 96 well culture plates. The compounds (0.16–16 μg/ml) were added to the cells 2 hours prior to RSVA$_2$ infection (~500 PFU/well) and the plates were stained with crystal violet 3 days after infection to reveal the cytopathic effects. Antiviral activities were determined in triplicate, while cellular toxicities were determined in a single test. The anti-flu activities of Compounds 1 and 2 against FluA/WSN were similarly determined in Madin Darby Canine Kidney (MDCK) cells except ~25 PFU of the virus were used and the plates were stained 2 days after infection. Compounds 1 and 2 were inactive against FluA/WSN.

The test data for anti-RSV are shown in Table 2.

TABLE 2

Formula I Compound Anti-RSV Test Data

| Compound | Anti-RSVA$_2$ ED$_{50}$, μg/ml | Cellular Toxicity TD$_{50}$, μg/ml |
|---|---|---|
| 1 | 0.05 | >16 |
| 2 | 0.05 | >16 |
| 3 | 1.6–5 | >16 |
| 4 | 0.16 | >16 |
| 5 | 1.6 | >16 |
| 6 | 5 | >16 |
| 7 | 1.6 | 16 |
| 8 | 0.005 | >16[a] |
| 9 | 1.6 | >16 |
| 10 | (0.05)[b] | >16 |
| 11 | 0.5 | >16 |
| 12 | 0.5 | >16 |
| 13 | (0.016)[c] | >16 |
| 14 | 0.5 | >16 |
| 15 | (0.05)[b] | >16 |
| 16 | (0.16)[b] | >16 |
| 17 | (0.016)[c] | >16 |
| Ribavirin | 1.6–5 | 50 |
| Amantadine | 50 | 100 |

[a] 20% cytotoxicity observed at ≧0.016 μg/ml
[b] No more than 50% protection at higher dose
[c] No more than 80% protection at higher dose The compounds of Examples 1 and 2 were active against both subgroup A (RSVA$_2$) and subgroup B (RSV-9320) of RSV in HEp-2 cells with an ED$_{50}$ 10- to 30-fold less than that of ribavirin and 100- to 300-fold less than that of amantadine. The results are shown in Table 3.

TABLE 3

Comparison of Examples 1 and 2, Amantadine and Ribavirin for Anti-RSV Activity in HEp-2 Cells

| Compound | Median Inhibitory Concentration (IC$_{50}$, μg/ml) Respiratory Syncytial Virus | |
|---|---|---|
| | RSVA$_2$ | RSV-9320 |
| Ex. 1 | ≦0.16 | ≦0.16 |
| Ex. 2 | ≦0.16 | ≦0.16 |
| Amantadine | 50 | 16 |
| Ribavirin | 1.6–5 | 5 |

The cytotoxic activities for the compounds of Examples 1 and 2, amantadine and ribavirin were determined in five different cell lines. The test results are summarized in Table 4.

TABLE 4

Comparison of Invention Compounds, Amantadine and Ribavirin for Cellular Toxicity

| Compound | Minimal Toxic Dose (μg/ml) that Inhibits All Growth | | | | |
|---|---|---|---|---|---|
| | MDCK | HEp-2 | A549 | MRC-5 | Vero |
| Ex. 1 | >100 | >100 | >100 | 100 | >100 |
| Ex. 2$^a$ | >50 | 50 | >50 | >50 | >50 |
| Amantadine | >100 | 100 | >100 | 100 | 100 |
| Ribavirin | 100 | 50 | 100 | 100 | 100 |

$^a$Not completely soluble at 100 μg/ml

Based on the in vitro anti-respiratory syncytial virus test data of the invention compounds as compared with ribavirin, the contemplated dosage of a Formula I compound for intranasal or intrabronchial administration is 10 to 30 times less than that of ribavirin. Oral or parenteral dosage forms may be given in one dose or divided doses. The exact dosage will, of course, be determined according to standard medical principles by a physician, beginning with a low dose and increasing the dosage until the desired antiviral effect is obtained.

The compounds may be administered neat or with a pharmaceutical carrier to a mammal in need thereof. The pharmaceutical carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredients. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g., glycols) and their derivatives, and oils (e.g., fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant.

For administration by intranasal or intrabronchial inhalation or insufflation, compounds of this invention can be formulated into an aqueous or partly aqueous solution, which can then be utilized in the form of an aerosol.

Liquid pharmaceutical compositions which are sterile solutions or suspensions can be utilized by, for example, intramuscular, intraperitoneal or subcutaneous injection. Sterile solutions can also be administrated intravenously. The compound can also be administered orally either in liquid or solid composition form.

What is claimed is:

1. A method of treating viral infections in mammals caused by respiratory syncytial virus which comprises administration to a mammal in need thereof a therapeutically effective amount of a compound of the formula:

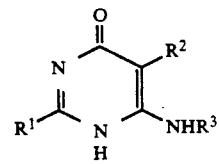

wherein:
R$^1$ is C$_1$-C$_6$ lower alkyl;
R$^2$ is halogen or cyano;
R$^3$ is C$_1$-C$_6$ alkyl or —(CH$_2$)$_n$R$^4$ where n is 1 or 2 and R$^4$ is phenyl, phenyl substituted by 1 to 2 groups selected from lower alkoxy, lower alkenyloxy, halogen, and methylenedioxy; pyridinyl, pyridinyl substituted by halogen or cyano, thienyl, or —NR$^1$R$^2$ when R$^1$ and R$^2$ are C$_1$-C$_6$ alkyl or —NR$^1$R$^2$ is a cyclic amine of 4–6 atoms;
or a pharmaceutically acceptable salt thereof.

2. The method according to claim 1 where, in the compound used, R$^1$ is methyl and R$^2$ is bromo, chloro, fluoro or cyano or a pharmaceutically acceptable salt thereof.

3. The method according to claim 2 where, in the compound used, R$^1$ is methyl and R$^2$ is bromo.

4. The method according to claim 3 where, in the compound used, R$^3$ is selected from 5-cyano-3-pyridinylmethyl, 2-(3-pyridinyl)ethyl, 2-(dipropylamino)ethyl, 3,4-methylenedioxyphenylmethyl, 3-thienylmethyl, 2-[3-methoxy-4-(2-propenyloxy)-phenyl]ethyl, 2(5-bromo-2-methoxyphenyl)ethyl, 3- methylbutyl, and 5-bromo-3-pyridinylmethyl or a pharmaceutically acceptable salt thereof.

5. The method according to claim 2 where, in the compound used, $R^2$ is cyano.

6. The method according to claim 5 where, in the compound used, $R^3$ is selected from 2-(3-pyridinyl)ethyl, 3-pyridinylmethyl, 2-(4-pyridinyl)ethyl, phenylmethyl, 2-(dimethylamino)ethyl, and 2-(1-pyrrolidinyl)ethyl or a pharmaceutically acceptable salt thereof.

7. The method according to claim 2 wherein the compound used is 6-[[(5-bromo-3-pyridinyl)methyl]amino]-5-chloro-2-methyl-4(1H)-pyrimidone or a pharmaceutically acceptable salt thereof.

8. The method according to claim 2 wherein the compound used is a 5-fluoro-2-methyl-6-[(3-pyridinylmethyl)amino]-4(1H)-pyrimidone or a pharmaceutically acceptable salt thereof.

9. The method according to claim 1 where, in the compound used, $R^1$ is t-butyl.

10. The method according to claim 9 wherein the compound used is 5-cyano-2-(1,1-dimethylethyl)-6-[(3-pyridinylmethyl)amino]-4(1H)-pyrimidone or a pharmaceutically acceptable salt thereof.

* * * * *